United States Patent
Allegretti et al.

(10) Patent No.: US 6,770,781 B1
(45) Date of Patent: Aug. 3, 2004

(54) PROCESS FOR THE PREPARATION OF ALPHA-ARYLALKANOIC ACIDS

(75) Inventors: Marcello Allegretti, L'Aquila (IT); Maria Candida Cesta, L'Aquila (IT); Marco Mantovanini, L'Aquila (IT); Luca Nicolini, L'Aquila (IT)

(73) Assignee: Dompe' S.p.A, L'Aquila (IT)

( * ) Notice: Subject to any disclaimer, the term of this patent is extended or adjusted under 35 U.S.C. 154(b) by 0 days.

(21) Appl. No.: 09/830,449

(22) PCT Filed: Oct. 18, 1999

(86) PCT No.: PCT/EP99/07887

§ 371 (c)(1),
(2), (4) Date: May 8, 2002

(87) PCT Pub. No.: WO00/26176

PCT Pub. Date: May 11, 2000

(30) Foreign Application Priority Data

Oct. 30, 1998 (IT) .......................................... MI98A2332

(51) Int. Cl.$^7$ ........................ C07C 57/30; C07C 51/255
(52) U.S. Cl. ...................................... 562/496; 562/418
(58) Field of Search ................................ 562/496, 418

(56) References Cited

U.S. PATENT DOCUMENTS 4,605,758 A * 8/1986 Schloemer .................. 562/418
4,910,337 A * 3/1990 Chiu et al. .................. 562/496
5,061,629 A * 10/1991 Coffen et al. ................ 435/280

FOREIGN PATENT DOCUMENTS

| GB | 971700 | * | 9/1964 |
| GB | 2025397 | | 1/1980 |
| GB | 1586798 | * | 3/1981 |
| WO | 9805623 | | 2/1998 |

OTHER PUBLICATIONS

McKay et al., *Can. J. Chem.*, 38, pp.2042–2052 (1960).
Newman et al., Journal of Organic Chemistry, vol. 31, No. 12, pp. 3980–3984 (1966).

* cited by examiner

Primary Examiner—Ba K. Trinh
Assistant Examiner—Taylor V Oh
(74) Attorney, Agent, or Firm—Birch, Stewart, Kolasch & Birch, LLP

(57) ABSTRACT

A process for the preparation of meta or para-substituted α-arylalkanoic acids of formula (I)

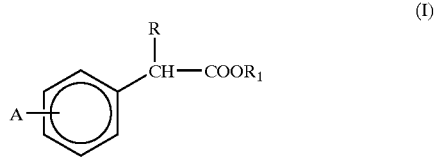

wherein R and $R_1$ are as defined in the disclosure.

9 Claims, No Drawings

PROCESS FOR THE PREPARATION OF ALPHA-ARYLALKANOIC ACIDS

This application is the national phase under 35 U.S.C. § 371 of PCT International Application No. PCT/EP99/07887 which has an International filing date of Oct. 18, 1999, which designated the United States of America and was published in English.

The present invention relates to a process for the preparation of meta or para-substituted α-arylalkanoic acids.

More particularly, the invention relates to a process for the preparation of compounds of formula (I)

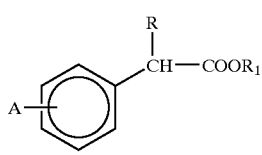
(I)

wherein

R is hydrogen, $C_1$–$C_6$ alkyl; $R_1$ is hydrogen, straight or branched $C_1$–C6 alkyl, phenyl, p-nitrophenyl, a cation of an alkali or alkaline-earth metal cation or of a pharmaceutically acceptable ammonium salt; A is $C_1$–$C_4$ alkyl, aryl, aryloxy, arylcarbonyl, 2-, 3- or 4-pyridocarbonyl, aryl optionally substituted with one or more alkyl, hydroxy, amino, cyano, nitro, alkoxy, haloalkyl, haloalkoxy; A is at the meta or para positions; starting from compounds of formula (II)

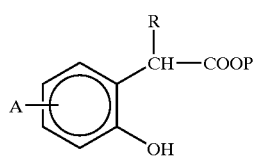
(II)

in which P is straight or branched $C_1$–$C_6$ alkyl, phenyl, p-nitrophenyl.

Different strategies are at present used for removing the phenolic hydroxyl of arylalkanoic acids derivatives, based on the derivatization and subsequent elimination of the derivative by reduction, but in most cases such procedures suffer from drawbacks such as high-cost reagents or lack of selectivity.

British Patent 2025397 (Chinoin), discloses the use of various derivatives of the phenolic hydroxyl, such as phenylaminocarbonyl, 1-phenyl-5-tetrazolyl, 2-benzoxazolyl, —$SO_2$OMe, and the reduction of the derivative with hydrogen on Pd/C catalyst.

WO 98/05632 application, in the Applicant's name, discloses the use of perfluoroalkanesulfonates, in particular trifluoromesylate, followed by reduction with formic acid and triethylamine in the presence or palladium acetate/triohenylphosphine complex.

It has now been found a process for the preparation of arylpropionic acids starting from the corresponding α-hydroxylated derivatives, using inexpensive reagents and keeping intact any reducible groups, such as esters or ketones, present on the side chains of the starting molecules.

According to the process of the invention, the compounds of formula (I) are prepared through the following steps:

a) transformation of compounds of formula (II) into compounds of formula (III):

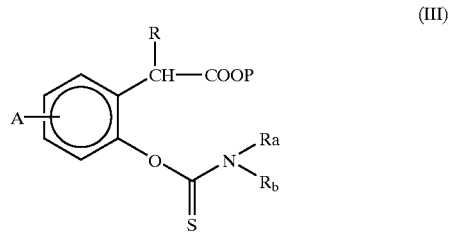
(III)

wherein $R_a$ and $R_b$ are $C_1$–$C_6$ alkyl, preferably methyl;

b) thermal rearrangement of compound (III) to give (IIIb)

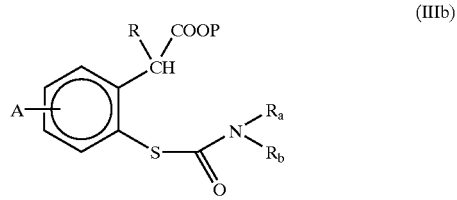
(IIIb)

c) catalytic hydrogenation of (IIIb) to give (IIIc)

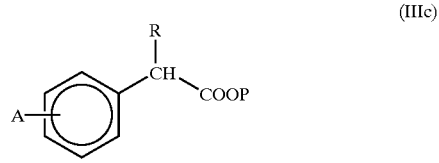
(IIIc)

d) transformation of (IIIc) into (I).

The compounds of formula (II) can be prepared as described in WO 98/05623. Briefly, starting from arylolefins of formula (IV)

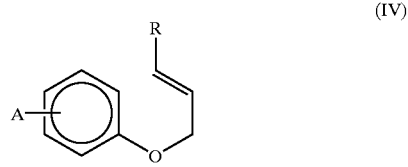
(IV)

wherein A and R have the same meanings as defined above, by Claisen rearrangement, compound (V) is obtained

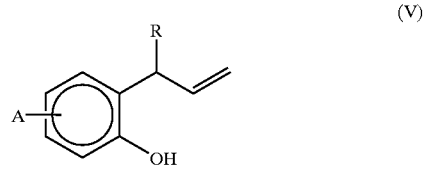
(V)

which can be subsequently subjected to oxidative cleavage, for example by ozonolysis or with potassium permanganate in phase transfer conditions, thus yielding the corresponding carboxylic acid product. The latter can be transformed into compound (II) by esterification with a suitable alcohol.

Step a) can be carried out in two ways.

In the first case, compound of formula (II) is reacted with

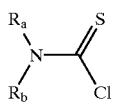

wherein $R_a$ and $R_b$ are as defined above, in the presence of an inorganic base such as an alkali or alkaline-earth carbonate, or an organic one, such as triethylamine or pyridine.

Alternatively, compound of formula (II) is reacted first with thiophosgene,

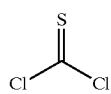

to obtain compound (IIIa)

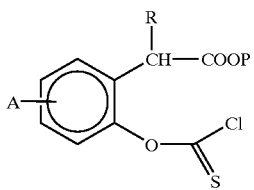

(IIIa)

which is subsequently reacted with $HNR_aR_b$ in which $R_a$ and $R_b$ are as defined above.

The conversion of the phenol in O-aryl-dialkylthiocarbamate by reaction with $R_bR_aNCSCl$, and the subsequent thermal rearrangement (step b) of the O-aryl dialkylthiocarbamate to give compound (IIIb), are described in Newman and Karnes, "The conversion of phenols", J. Org. Chemistry, Vol. 31, 1966, 3980–3982.

On the ocher hand, as for the preparation of the O-aryl-dialkylthiocarbamate by reacting the phenol with thiophosgene and subsequently the resulting product with amine $R_aR_bNH$, the method reported in Can. J. Chem., 38, 2042–52 (1960) can be followed.

In step c), the catalytic hydrogenation of S-aryl-dialkylthiocarbamate (IIIb) to give (IIIc) can be carried out with Ni-Raney as catalyst.

Compound (IIIc) is easily converted to (I) through conventional procedures for the hydrolysis of the ester group and optional subsequent reesterification or salification of the carboxylic group.

The process of the invention proved to be particularly advantageous when group A in general formula (I) is an optionally substituted aroyl group, in that the carbonyl function is preserved during the reduction of the thiocarbamoyl derivative. For example, when A is benzoyl, no reduction of the ketone under the used experimental conditions is observed. Furthermore, as already mentioned, the process of the invention is based on the use of low cost reagents, provides good yields, requires no purifications of the intermediates and has a low environmental impact.

The following examples illustrate the invention in greater detail.

EXAMPLE 1

Preparation of 2-(3'-benzoyl-2'-hydroxyphenyl)-propionic acid methyl ester (2)

A solution of 2-(3'-benzoyl-2'-acetoxyphenyl)propionic acid (1) (6.2 g) in methanol (35 ml) was added wish concentrated $H_2SO_4$ (0.3 ml). The mixture was stirred at room temperature for 15 hours until disappearance (1) and of the reaction intermediates. The solvent was evaporated off under vacuum and the residue was dissolved in ethyl acetate (30 ml) and washed with water. The organic layer was treated with a NaOH solution (100 ml), and the basic phase was acidified with 4N HCl and extracted with ethyl acetate (2×25 ml). The collected organic layers were washed with brine, dried over $Na_2SO_4$ and evaporated under vacuum. The crude product (4.3 g) was dissolved in isopropyl ether (5 ml) and the slightly yellow precipitate was filtered. n-Hexane (25 ml) was added to the residue and the mixture was stirred overnight. After filtration, 3.2 g of (2) were obtained (0.11 mol; 70% yield starting from 4) as a whitish solid (melting point 108–111° C.).

TLC ($CH_2Cl_2$/MeOH 9:1 Rf=0.45).

Elementary analysis calculated for $C_{17}H_{16}O_3$: C-71.81, H-5.67.

Found: C-71.16, H-5.63.

$^1$H-NMR (CDCl$_3$) d 8.4 (s, OH, 1H); 7.85–7.3 (m, 7H); 7.0 (d, 1H, J=7 Hz); 3.95 (q, 1H, 8 Hz); 3.8 (s, 3H); 1.6 (d, 3H, J=8 Hz).

EXAMPLE 2

Preparation of 2-(3'-benzoyl-2'-O-dimethylthiocarbamoylphenyl)-propionic acid methyl ester (3)

A solution of (2) (3.2 g, 0.011 mol) in acetone (25 ml) was added with potassium carbonate (1.65 g, 0.012 mol) and the mixture was stirred at room temperature for 15 min. A solution of N,N-dimetilcarbamoyl chloride (1.51 g, 0.012 mol) in acetone (5 ml) was added drop by drop to the refluxed mixture for 2 hours. After cooling at room temperature, the precipitated inorganic salts were filtered off and the solvent was evaporated under vacuum. The residue was dissolved in ethyl acetate (25 ml) and washed with water (2×10 ml) and brine (2×10 ml). The organic phase was dried over $Na_2SO_4$ and evaporated under vacuum, to obtain 3.45 g of (3) as a dark oil sufficiently pure to be used in the subsequent step.

TLC (n-hexane/EtOAc 8:2) Rf=0.25.

Elementary analysis calculated for $C_{20}H_{22}NO_4S$: C-64.49, H-5.95, N-3.76, S-8.61.

Found: C-64.17, H-5.92, N-3.82, S-8.60.

$^1$H-NMR (CDCl$_3$) d 7.95–7.8 (m, 4H); 7.6–7.4 (m, 3H); 7.2 (d, 1H, J=7 Hz); 3.9 (q, 1H, J=8 Hz); 3.7 (s, 3H); 3.6 (s, 3H); 3.4 (s, 3H) 1.6 (d, 3H, J=8 Hz).

EXAMPLE 3

Preparation of 2-(3'-benzoyl-2'-S-dimethylthiocarbamoylphenyl)propionic acid methyl ester (4)

Compound (3) (3.45 g) was heated in a flask at T=210° C. (temperature of the outer oil bath) for 2 hours under stirring. After cooling at room temperature and evaporation under vacuum, 3.45 g of (4) was obtained (0.0054 mol) sufficiently pure to be used without further purifications.

TLC (n-hexane/ethyl acetate 8:2 Rf=0.2).

Elementary analysis calculated for $C_{20}H_{22}NO_4S$: C-64.49, H-5.93, N-3.76, S-8.61.

Found: C-64.17, H-5.92, N-3.82, S-8.60.

$^1$H-NMR (CDCl$_3$) d 7.9–7.8 (m, 3H); 7.7–7.3 (m, 5H); 4.4 (q. 1H, J=8 Hz); 3.65 (s, 3H); 3.2–2.9 (d broad, 6H); 1.6 (d, 3H, J=8 Hz).

EXAMPLE 4

Preparation of 2-(3'-benzoylphenyl)-propionic acid methyl ester (5)

Acetone (50 ml) was added to Ni-Raney (50% in water, 20 ml) and the water/acetone mixture was removed. The treatment was repeated 3 times. Subsequently the catalyst was suspended in acetone (30 ml) and refluxed for 30 hours.

A solution of (4) (3.45 g) in acetone (4 ml) was added drop by drop and the mixture was refluxed overnight. After cooling at room temperature, the catalyst was filtered off and washed with acetone (10 ml). The filtrate was evaporated under vacuum, to obtain 2.4 g of (5) as a slightly brown oil.

TLC (n-hexane/ethyl acetate 9:1 Rf=0.7).

Elementary analysis calculated for $C_{17}H_{16}O_3$: C-76.10, H-6.01.

Found: C-75.99, H-6.03.

$^1$H-NMR (CDCl$_3$) d 7.9–7.4 (m, 8H); 3.8 (q, 1H, J=8 Hz); 3.65 (s, 3H); 1.6 (d, 3H, J=8 Hz).

EXAMPLE 5

Preparation of 2-(3'-benzoylphenyl)propionic acid (6)

The solution of (5) (2.4 g, 0.009 mol) in methyl alcohol (25 ml) was added with 1N NaOH (13.5 ml) and the mixture was left under stirring for 8 hours at room temperature. After evaporating the solvent, the residue was diluted with water and 5% monobasic sodium phosphate was added drop by drop to the mixture to adjust pH to 5. The aqueous layer was then extracted with methyl acetate (2×100 ml). The collected organic extracts were dried over $Na_2SO_4$ and evaporated under vacuum, then crystallized from a benzene/petroleum ether 6:20 mixture to obtain 2.05 g of (6) (0.0081 mol; yield 90%) as a white solid (melting point 92–92° C.) following crystallization.

TLC (CHCl$_3$/CH$_3$OH 95:5) Rf=0.2.

Elementary analysis calculated for $C_{16}H_{14}O_3$: C-75.57, H-5.55.

Found: C-75.19, H-5.53.

$^1$H-NMR (CDCl$_3$) d 7.91–7.75 (d, 3H), 7.74–7.51 (m, 2H), 7.50–7.35 (m, 4H), 3.85 (q, 1H, J=10 Hz), 1.58 (d, 3H, J=10 Hz).

What is claimed is:

1. A process for the preparation of meta or para-substituted α-arylalkanoic acids of formula (I):

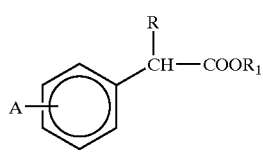

(I)

wherein

R is hydrogen; $C_1$–$C_6$ alkyl; $R_1$ is hydrogen, straight or branched $C_1$–C6 alkyl, phenyl, p-nitrophenyl, a cation of an alkali or alkaline-earth metal cation or of a pharmaceutically acceptable ammonium salt; A is $C_1$–$C_4$ alkyl, aryl, aryloxy, arylcarbonyl, 2-, 3- or 4-pyridcarbonyl, aryl optionally substituted with one or more alkyl, hydroxy, amino, cyano, nitro, alkoxy, haloalkyl, haloalkoxy; A is at the meta or para positions; which process comprises the following steps:

a) reaction of compounds of formula (II)

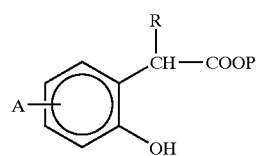

(II)

in which P is straight or branched $C_1$–$C_6$ alkyl, phenyl, p-nitrophenyl, with a thiocarbonyl halide to give compounds of formula (III)

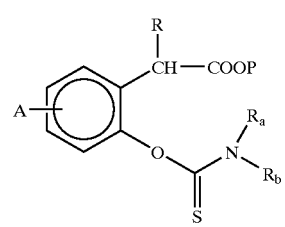

(III)

wherein $R_a$ and $R_b$ are $C_1$–$C_6$ alkyl, b) thermal rearrangement of compound (III) to give (IIIb)

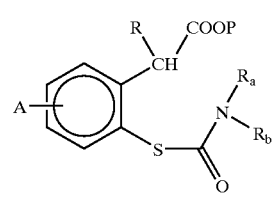

(IIIb)

c) catalytic hydrogenation of (IIIb) to give (IIIc)

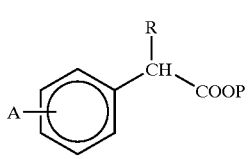

(IIIc)

d) hydrolysis of (IIIc) and optional subsequent reesterfication or salification to give (I).

2. A process according to claim 1, in which the transformation of step a) is carried out by reaction of the compound (II) with

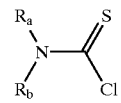

wherein $R_a$ and $R_b$ are as defined in claim 1, in the presence of an organic or inorganic base.

3. A process as claimed in claim 2, in which said organic base is selected from triethylamine and pyridine, and said inorganic base is selected from alkali or alkaline-earth carbonates.

4. A process as claimed in claim 1, in which the transformation of step a) is carried out by reaction of compound (II) with thiophosgene

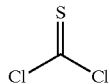

and the subsequent reaction of the resulting product with $HNR_aR_b$, wherein $R_a$ and $R_b$ are as defined in claim 1.

5. A process as claimed in claim 1, in which the hydrogenation of step c) is carried out with Ni-Raney.

6. A process according to any one of the above claims, in which the group A of formula (I) is meta-benzoyl and R is methyl.

7. As a reaction intermediate, the compound

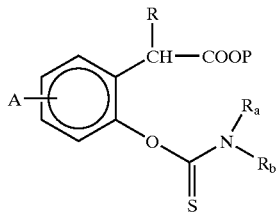

(III)

wherein
R is hydrogen, $C_1$–$C_6$ alkyl; A is a $C_1$–$C_4$ alkyl, aryl, aryloxy, aryl optionally substituted with one or more alkyl, hydroxy, amino, cyano, nitro, alkoxy, haloalkyl, haloalkoxy, A is at the meta or para positions; P is straight or branched $C_1$–$C_6$ alkyl, phenyl, p-nitrophenyl; $R_a$ and $R_b$ are $C_1$–$C_6$ alkyl.

8. As a reaction intermediate, the compound

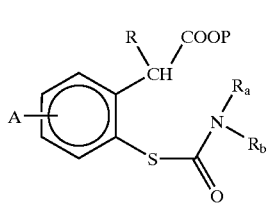

(IIIb)

wherein A, R, P, $R_a$ and $R_b$ are as defined in claim 7.

9. A process for the preparation of meta or para-substituted α-arylalkanoic acids of formula (I):

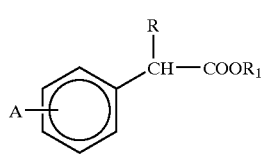

(I)

wherein R is hydrogen; $C_1$–$C_6$ alkyl; $R_1$ is hydrogen, straight or branched $C_1$–$C_6$ alkyl, phenyl, p-nitrophenyl, a cation of an alkali or alkaline-earth metal cation or of a pharmaceutically acceptable ammonium salt; A is $C_1$–$C_4$ alkyl, aryl, aryloxy, arylcarbonyl, 2-, 3- or 4-pyridocarbonyl, aryl optionally substituted with one or more alkyl, hydroxy, amino, cyano, nitro, alkoxy, haloalkyl, haloalkoxy; A is at the meta or para positions;

wherein said process comprises the steps of:
a) reaction of compounds of formula (II)

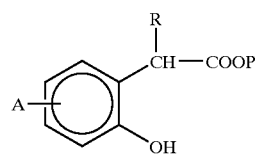

(II)

in which P is straight or branched $C_1$–$C_6$ alkyl, phenyl, p-nitrophenyl, with the compound

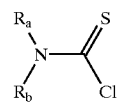

wherein $R_a$ and $R_b$ are $C_1$–$C_6$ alkyl, in the presence of an organic or inorganic base, or
with a thiophosgene

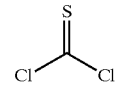

and the subsequent reaction of the resulting product with $HNR_aR_b$, wherein $R_a$ and $R_b$ are as defined above, to give compounds of formula (III)

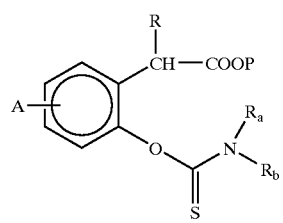

(III)

wherein $R_a$ and $R_b$ are as defined above,
b) thermal rearrangement of compound (III) to give (IIIb)

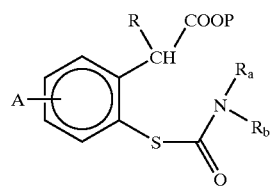

(IIIb)

c) catalytic hydrogenation of (IIIb) to give (IIIc)

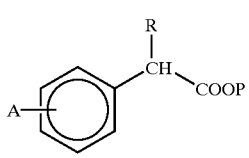

(IIIc)

d) hydrolysis of (IIIc) and optional subsequent reesterification or salification to give (I).

* * * * *